US012121421B2

(12) United States Patent
Donda et al.

(10) Patent No.: US 12,121,421 B2
(45) Date of Patent: *Oct. 22, 2024

(54) WOUND THERAPY DEVICE AND METHOD

(71) Applicant: Aatru Medical, LLC, Cleveland, OH (US)

(72) Inventors: Russell S. Donda, North Royalton, OH (US); Sundar Manickam, Avon, OH (US); Richard L. Middaugh, Rocky River, OH (US); Thomas E. Lash, Chardon, OH (US); Timothy Wojciechowski, Westlake, OH (US); John D. Wolter, Berea, OH (US); John Buan, Maple Grove, MN (US)

(73) Assignee: AATRU MEDICAL, LLC, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/231,349

(22) Filed: Aug. 8, 2023

(65) Prior Publication Data

US 2023/0381027 A1 Nov. 30, 2023

Related U.S. Application Data

(63) Continuation of application No. 17/351,749, filed on Jun. 18, 2021, now Pat. No. 11,759,368, which is a
(Continued)

(51) Int. Cl.
*A61F 13/05* (2024.01)
*A61F 13/00* (2024.01)
(Continued)

(52) U.S. Cl.
CPC .............. *A61F 13/05* (2024.01); *A61F 13/00* (2013.01); *A61F 13/00063* (2013.01);
(Continued)

(58) Field of Classification Search
CPC ...... A61M 1/00; A61M 1/0066; A61M 1/009; A61M 1/08; A61M 1/34; A61L 15/00; A61L 15/16; A61L 15/42; A61L 15/52
See application file for complete search history.

(56) References Cited

U.S. PATENT DOCUMENTS 3,849,528 A * 11/1974 Smith .................. D06N 3/0052
521/159
5,578,022 A 11/1996 Scherson et al.
(Continued)

FOREIGN PATENT DOCUMENTS

JP 2007509639 4/2007
JP 2011513003 4/2011
(Continued)

OTHER PUBLICATIONS

Japanese Office Action of S/N 2020-009747 dated Mar. 16, 2021, 4 pages.
(Continued)

*Primary Examiner* — Guy K Townsend
(74) *Attorney, Agent, or Firm* — RANKIN, HILL & CLARK LLP

(57) ABSTRACT

A wound therapy device and method includes a skin contacting element, a reactor, and a reactor housing element. The skin contacting element is configured for covering an associated tissue site, the reactor for creating a pressure condition at the associated tissue site upon actuation thereof, and the reactor housing element for accommodating the reactor. The skin contacting element has a skin contacting side and an interface side, which is opposite the skin contacting side. The reactor housing element has a lower affixing side and an upper side, which is opposite the lower affixing side.

16 Claims, 5 Drawing Sheets

Related U.S. Application Data continuation of application No. 16/561,121, filed on Sep. 5, 2019, now Pat. No. 11,071,652, which is a continuation of application No. 15/771,843, filed as application No. PCT/US2016/059364 on Oct. 28, 2016, now Pat. No. 10,449,094.

(60) Provisional application No. 62/248,422, filed on Oct. 30, 2015.

(51) Int. Cl.
*A61F 13/02* (2024.01)
*A61H 9/00* (2006.01)
*A61M 1/00* (2006.01)
*A61M 27/00* (2006.01)
*A61M 35/00* (2006.01)
*A61M 37/00* (2006.01)
*A61N 1/04* (2006.01)
*A61N 1/36* (2006.01)
*A61N 5/06* (2006.01)

(52) U.S. Cl.
CPC ........... *A61F 13/02* (2013.01); *A61H 9/0057* (2013.01); *A61H 9/0071* (2013.01); *A61M 1/60* (2021.05); *A61M 1/80* (2021.05); *A61M 1/92* (2021.05); *A61M 1/962* (2021.05); *A61M 1/985* (2021.05); *A61M 27/00* (2013.01); *A61M 35/30* (2019.05); *A61M 37/00* (2013.01); *A61N 1/0492* (2013.01); *A61N 1/36014* (2013.01); *A61H 2201/0278* (2013.01); *A61H 2201/105* (2013.01); *A61H 2201/1238* (2013.01); *A61H 2201/165* (2013.01); *A61M 1/964* (2021.05); *A61M 2205/0277* (2013.01); *A61M 2205/051* (2013.01); *A61M 2205/054* (2013.01); *A61M 2205/364* (2013.01); *A61N 5/0616* (2013.01); *A61N 2005/0652* (2013.01)

(56) References Cited

U.S. PATENT DOCUMENTS

| | | | |
|---|---|---|---|
| 5,639,568 A | 6/1997 | Pedicini et al. | |
| 6,040,493 A | 3/2000 | Cooke et al. | |
| 6,336,935 B1 | 1/2002 | Davis et al. | |
| 6,465,709 B1 | 10/2002 | Sun et al. | |
| 6,669,966 B1* | 12/2003 | Antelman | A61P 35/00 |
| | | | 424/407 |
| 6,756,053 B2 | 6/2004 | Zhang et al. | |
| 6,767,342 B1 | 7/2004 | Cantwell | |
| 6,890,553 B1* | 5/2005 | Sun | A61F 7/034 |
| | | | 424/443 |
| 6,893,453 B2 | 5/2005 | Agarwal et al. | |
| 7,108,440 B1 | 9/2006 | Gruenbacher et al. | |
| 7,361,184 B2* | 4/2008 | Joshi | A61M 1/985 |
| | | | 602/42 |
| 7,457,667 B2 | 11/2008 | Skiba | |
| 7,615,036 B2 | 11/2009 | Joshi et al. | |
| 7,779,625 B2 | 8/2010 | Joshi et al. | |
| 7,922,676 B2 | 4/2011 | Daskal et al. | |
| 8,012,169 B2 | 9/2011 | Joshi | |
| 8,353,928 B2 | 1/2013 | Joshi | |
| 8,372,049 B2 | 2/2013 | Jaeb et al. | |
| 8,372,050 B2 | 2/2013 | Jaeb et al. | |
| 8,439,894 B1* | 5/2013 | Miller | A61M 1/985 |
| | | | 604/319 |
| 8,449,508 B2 | 5/2013 | Coulthard et al. | |
| 8,460,255 B2 | 6/2013 | Joshi et al. | |
| 8,569,566 B2* | 10/2013 | Blott | A61F 13/0206 |
| | | | 602/41 |
| 8,586,818 B2 | 11/2013 | Aali | |
| 8,915,895 B2 | 12/2014 | Jaeb et al. | |
| 9,050,209 B2 | 6/2015 | Coulthard et al. | |
| 9,168,330 B2 | 10/2015 | Joshi et al. | |
| 9,446,178 B2* | 9/2016 | Blott | A61M 1/82 |
| 9,452,248 B2* | 9/2016 | Blott | A61M 1/962 |
| 9,480,830 B1 | 11/2016 | Azocar | |
| 9,882,196 B2 | 1/2018 | Eaglesham et al. | |
| 10,046,095 B1 | 8/2018 | Middaugh | |
| 10,449,094 B2* | 10/2019 | Donda | A61M 1/92 |
| 11,071,652 B2* | 7/2021 | Donda | A61M 1/94 |
| 11,759,368 B2* | 9/2023 | Donda | A61F 13/02 |
| | | | 604/543 |
| 2001/0020145 A1 | 9/2001 | Satterfield et al. | |
| 2003/0162095 A1 | 8/2003 | Huang et al. | |
| 2005/0070835 A1* | 3/2005 | Joshi | A61M 1/962 |
| | | | 602/41 |
| 2006/0235358 A1* | 10/2006 | Azocar | A61F 13/01021 |
| | | | 604/304 |
| 2008/0082069 A1 | 4/2008 | Qin et al. | |
| 2008/0183119 A1* | 7/2008 | Joshi | A61M 1/962 |
| | | | 602/42 |
| 2008/0188820 A1* | 8/2008 | Joshi | A61M 1/962 |
| | | | 604/304 |
| 2009/0131888 A1* | 5/2009 | Joshi | A61M 1/985 |
| | | | 604/290 |
| 2009/0202617 A1 | 8/2009 | Ward et al. | |
| 2009/0227969 A1* | 9/2009 | Jaeb | A61M 1/985 |
| | | | 604/313 |
| 2010/0217177 A1* | 8/2010 | Cali | A61P 17/02 |
| | | | 604/23 |
| 2010/0305490 A1* | 12/2010 | Coulthard | A61F 13/022 |
| | | | 604/313 |
| 2011/0045222 A1 | 2/2011 | Peters | |
| 2012/0010579 A1* | 1/2012 | Joshi | A61M 1/985 |
| | | | 604/317 |
| 2012/0123373 A1* | 5/2012 | Melik | A61L 15/24 |
| | | | 604/372 |
| 2012/0253152 A1 | 10/2012 | Haisley et al. | |
| 2012/0253159 A1 | 10/2012 | Medina et al. | |
| 2013/0116612 A1 | 5/2013 | Stephan | |
| 2014/0107562 A1 | 4/2014 | Dorian et al. | |
| 2014/0109890 A1 | 4/2014 | Pedicini et al. | |
| 2015/0057625 A1 | 2/2015 | Coulthard | |
| 2015/0174304 A1* | 6/2015 | Askem | A61F 13/0246 |
| | | | 604/319 |
| 2015/0191845 A1* | 7/2015 | Scherson | H01J 7/18 |
| | | | 417/48 |
| 2016/0120176 A1* | 5/2016 | Sanghi | A61F 13/00063 |
| | | | 521/53 |
| 2017/0056405 A1 | 3/2017 | Sun et al. | |
| 2017/0304510 A1* | 10/2017 | Askem | A61M 1/964 |
| 2018/0042928 A1 | 2/2018 | Sun et al. | |
| 2018/0105948 A1* | 4/2018 | Scherson | C25D 17/00 |
| 2018/0153768 A1* | 6/2018 | Hemmrich | A61K 33/00 |
| 2018/0318137 A1* | 11/2018 | Donda | A61M 1/962 |
| 2018/0318165 A1 | 11/2018 | Donda et al. | |
| 2019/0091381 A1* | 3/2019 | Askem | A61M 1/962 |
| 2019/0388278 A1* | 12/2019 | Donda | A61M 1/92 |
| 2021/0353470 A1* | 11/2021 | Donda | A61M 1/80 |
| 2023/0381027 A1* | 11/2023 | Donda | A61F 13/02 |

FOREIGN PATENT DOCUMENTS

| | | |
|---|---|---|
| JP | 2015054040 | 3/2015 |
| JP | 2015514451 | 5/2015 |
| WO | 01/03619 | 1/2001 |
| WO | 2007070151 | 6/2007 |
| WO | 2009151380 | 12/2009 |
| WO | 2013136181 | 9/2013 |
| WO | 2015054040 | 4/2015 |

OTHER PUBLICATIONS

Brazilian Preliminary Office Action of BR 112018008402-6 dated May 26, 2020, 5 pages.
Japanese Office Action of S/N 2018-542985 dated Dec. 3, 2019, 3 pages.

(56) References Cited

OTHER PUBLICATIONS

International Search Report and Written Opinion of PCT/US2016/059291 dated Feb. 28, 2017, 16 pages.
International Search Report and Written Opinion of PCT/US2016/059364 dated Mar. 29, 2017, 17 pages.
Extended European Search Report of EP 16 86 0896 dated Jun. 4, 2019, 7 pages.
Supplementary EP Search Report of EP 16 86 0863 dated Jun. 24, 2019, 1 page.

* cited by examiner

WOUND THERAPY DEVICE AND METHOD

This application claims priority to U.S. Provisional Application Ser. No. 62/248,422 filed on Oct. 30, 2015, the entirety of which is expressly incorporated by reference.

BACKGROUND

Negative pressure is a term used to describe a pressure that is below normal atmospheric pressure. At room temperature and at sea level, a defined volume of air contains molecules moving in random directions, and these moving molecules exert a force that is equal to the normal atmospheric pressure of approximately 756 mmHg (about 1 bar). Negative pressure has been achieved by removing air from an area of interest, for example at a wound site via a suction pump. Devices for the generation of topical negative pressure at the surface of a subject's skin have been used for many hundreds of years to treat humans. For example, the cupping technique, which relates to positioning a mouth of a rigid vessel containing hot air on a human's skin, is a well-known technique. Spring powered syringes and suction cups are other mechanical techniques that have been used for generating a vacuum on human tissue. In common with cupping, such other mechanical techniques have offered a limited topical negative pressure duration and little or no range of neutral to positive pressures. This is due to design constraints and that the cupping technique and other mechanical techniques are not self-contained and can hinder a user's mobility.

Known topical negative pressure devices range from cumbersome wrinkle reducing suction apparatuses to wound therapies that include fluid-permeable wound cavity filling elements, covering dressings, reasonably air-tight means for sealing against the skin, and drainage tubes connecting the wound site and cavity filling element to the vacuum source via a fluid collection canister. The mode of action of such devices is the application of negative pressure to the tissue site, causing an expansion of the enclosed tissue into the cavity enabled by sealing the apparatus against the skin. When the treated tissue site is a wound, exudate can be drawn from the surrounding tissue through the porous cavity filler, into the drainage tube and then into a remote collection receptacle. A consideration of such known devices is the ability of the wound cavity filler to remain sufficiently porous so that, when compressed under negative pressure, fluid may be transported from the tissue site to a drainage or aspirant tube.

To enable a more prolonged application of topical negative pressure, powered systems, which include a vacuum generation source such as a pump, have been developed and many examples of such systems are used today for skin treatments and restorative purposes like the temporary removal of wrinkles. Many of these systems, however, are not convenient for users. Such known systems can be large, heavy, noisy, uncomfortable, and not simple for users to apply and initiate a controlled pressure condition. Such known systems also rely on an outside power or vacuum source to create topical negative pressure conditions.

Such tissue treatment, surgery, and other advanced technical interventions are becoming more common given the occurrence of both the aging population, as well as increasingly compromised patient populations. This trend looks set to continue. In wound care, for example, healthcare professionals are now more likely to encounter wounds that are difficult to manage with complex healing problems. Attempts have been made to produce more simple mechanical devices able to apply topical and negative pressure to a tissue site. It will be appreciated that such a medical device, due to its relative simplicity of design, would be expected to reduce material costs and assembly costs. For example, attempts have been made to use a hand-pump system for the application of topical negative pressure at a tissue site. However, such a system fails to enable easier application by the user, discreet use, and prolonged convenient application of topical negative pressure, and, in fact, re-evacuation is often necessary. These can be serious deficiencies, particularly as many such systems are ideally useable for prolonged periods, such as overnight.

SUMMARY

According to one aspect, a wound therapy device includes a skin contacting element, a reactor, and a reactor housing element. The skin contacting element is configured for covering an associated tissue site, the reactor for creating a pressure condition at the associated tissue site upon actuation thereof, and the reactor housing element for accommodating the reactor. The skin contacting element has a skin contacting side and an interface side, which is opposite the skin contacting side. The reactor housing element has a lower affixing side and an upper side, which is opposite the lower affixing side. The reactor housing element is configured to be affixed to the skin contacting element after the reactor is actuated.

According to another aspect, a wound therapy device includes a skin contacting element, a reactor, a reactor housing element and an air permeable liquid impervious membrane. The skin contacting element is configured for covering an associated tissue site, the reactor for creating a pressure condition at the associated tissue site upon actuation thereof, and the reactor housing element for accommodating the reactor. The skin contacting element has a skin contacting side and an interface side, which is opposite the skin contacting side. The reactor housing element has a lower affixing side and an upper side, which is opposite the lower affixing side. The air permeable liquid impervious membrane is arranged on an exposure side of the reactor so as to be interposed between the reactor and the skin contacting element when the reactor housing element is affixed to the skin contacting element.

According to still another aspect, a wound therapy device includes a skin contacting element, a reactor and a reactor housing element. The skin contacting element is configured for covering an associated tissue site, the reactor for creating a pressure condition at the associated tissue site upon actuation thereof, and the reactor housing element for accommodating the reactor. The skin contacting element has a skin contacting side and an interface side, which is opposite the skin contacting side. The reactor housing element has a lower affixing side and an upper side, which is opposite the lower affixing side. The reactor housing reactor housing element is removably affixed to the skin contacting element to enable removal of the reactor housing element and replacement of one or both of the reactor and the reactor housing element.

According to a further aspect, a method for applying controlled pressure to a tissue site includes: covering the tissue site with a skin contacting element; affixing a reactor housing element to the skin contacting element; and actuating a reactor to create a pressure condition at the tissue site. The skin contacting element has a skin contacting side and an interface side, which is opposite the skin contacting side. The covering of the tissue site with the skin contacting element includes the skin contacting side being arranged to face the tissue site. The reactor housing element has the reactor accommodated therein. The reactor housing element also has a lower affixing side and an upper side, which is opposite the lower affixing side. The affixing of the reactor housing element to the skin contacting element occurs after the actuating of the reactor.

DETAILED DESCRIPTION

Figure 1:
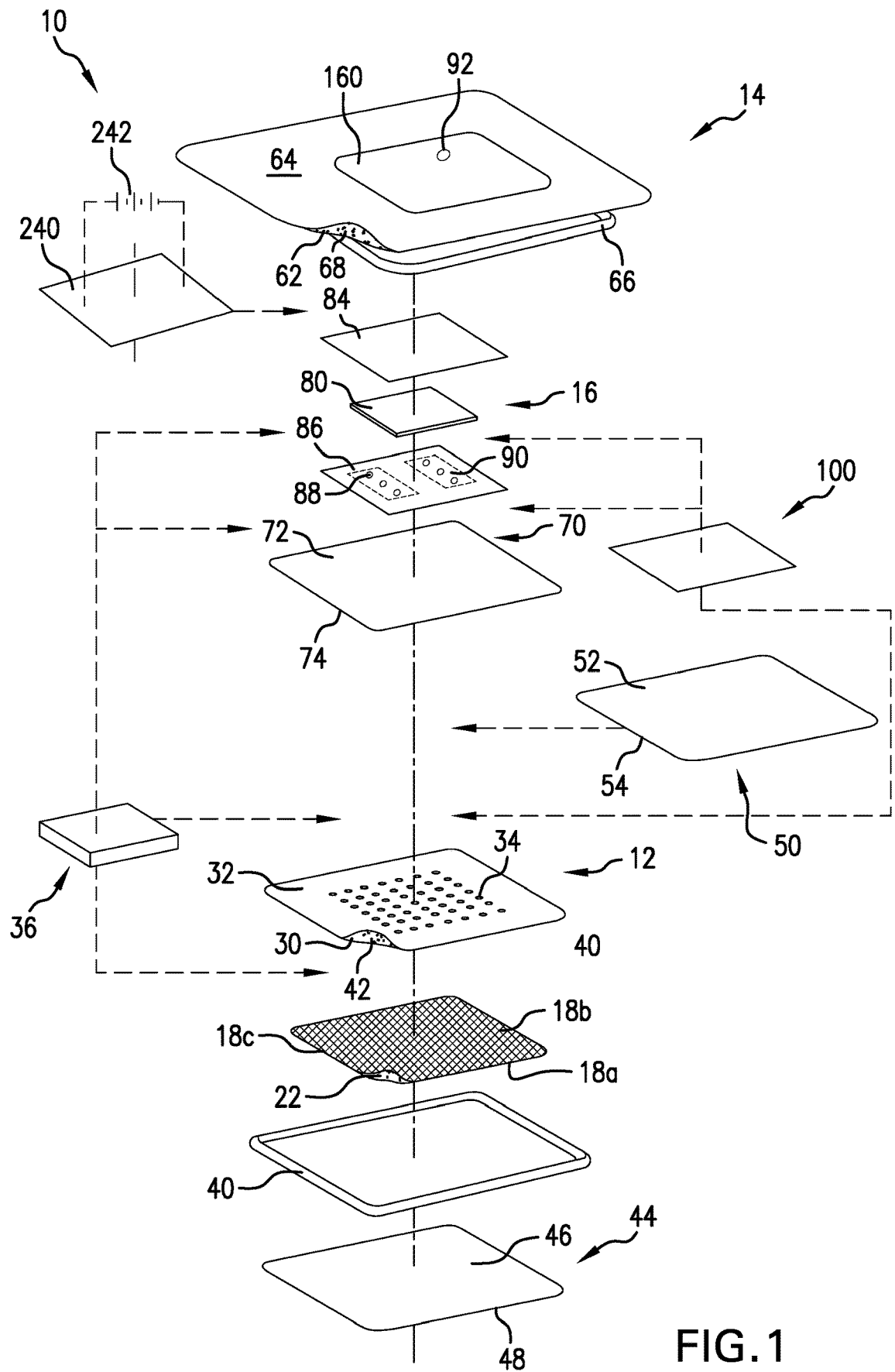
FIG. 1 is a schematic exploded perspective view of a controlled pressure device according to an exemplary embodiment.

FIG. 1 depicts a controlled pressure device 10, which can also be referred to as a wound therapy device or a self-contained wound therapy device, according to an exemplary embodiment. The wound therapy device 10 includes a skin contacting element 12, a reactor housing element 14, and a reactor 16. With additional reference to FIG. 2, the wound therapy device 10 can also include a wound contact element 18 for direct contact with a tissue site 20, and specifically for direct contact with a wound or treatment portion 20a at the tissue site 20. As will be described in more detail below, the wound therapy device 10 can be positioned at the tissue site 20 to enhance tissue treatment including, but not limited to, wound healing (e.g., healing of the wound portion 20a), reduction of skin wrinkles, other skin maladies, etc. As will be described in more detail below, the skin contacting element 12 is configured for covering the associated tissue site 20, and particularly for covering the wound portion 20a of the tissue site 20. As used herein, the tissue site is referred to as an associated tissue site so as to indicate that the tissue site itself (and the wound portion 20a of the tissue site) is not generally considered a component of the wound therapy device 10. The reactor housing element 14 is provided for accommodating the reactor 16 and the reactor 16 is provided for creating a pressure condition at the associated tissue site 20 upon actuation thereof (i.e., actuation of the reactor 16) for acting upon the wound portion 20a. The wound contact element 18 is provided for directly contacting a wound portion 20a at the tissue site 20 (i.e., the contact element 18 is interposed between the skin contact element 12 and the wound portion 20a).

In one embodiment, the reactor housing element 14 is configured to be affixed to the skin contacting element 12 after the reactor 16 is actuated. In the same or another embodiment, a liquid impermeable-air permeable membrane (e.g., membrane 100) can be provided to inhibit or limit exudate suctioned from the tissue site 20 from reaching the reactor 16. In these or a further embodiment, the skin contacting element 12 is configured to remain in place at a tissue site when the reactor element 14 is changed, for example when the reactor 16 is sufficiently used up and a new reactor 16 is desired. In these and other embodiments, the wound therapy device 10 is self-contained in that it does not need to be connected to an external power and/or vacuum source in contrast to many prior art devices.

The skin contacting element 12 includes a skin contacting side 30 that is adherable to a subject's skin (e.g., around the wound portion 20a) and an interface side 32, which is opposite to the skin contacting side 30. In the illustrated embodiment, the skin contacting element 12 is shown as a separate element from the reactor housing element 14. In an alternative arrangement, the skin contacting element 12 can be provided as part of the reactor housing element 14, e.g., the skin contacting element 12 can be integrally formed with the reactor housing element 14 or connected with the reactor housing element 14 at the manufacturing facility and the elements 12, 14 can be together applied to the tissue site 20. In the illustrated embodiment, the skin contacting element 12 is a flexible material (e.g., a thin gas impermeable film) that allows the wound therapy device 10 to conform to a subject's skin disposed at and/or around the tissue site 20. The skin contacting element 12 can be made from a thin sheet-like membrane (e.g., a thin gas impermeable film), for example using a roll-to-roll process.

Also in the illustrated embodiment, the skin contacting element 12 includes one or more openings 34, alternatively referred to herein as skin contacting element openings, extending through the skin contacting element 12 from the skin contacting side 30 to the interface side 32. The skin contacting element openings 34 can be arranged for positioning over the tissue site 20, and particularly over the wound portion 20a thereof, and further arranged such that the pressure condition created by the reactor 16 is applied to the tissue site 20, and particularly to the wound portion 20a, through the skin contacting element openings 34. The one or more openings 34 can be used to control or limit the speed of scavenging by the reactor 16. For example, the number of openings 34 and/or the size of the openings 34 (i.e., surface area of the openings) can effectively limit the amount of air that reaches the reactor 16 and thereby control the rate of consumption by the reactor 16. In addition to controlling the pressure condition created by the reactor 16, this can also control the amount or rate of heat produced by the reactor 16.

Figure 1A:
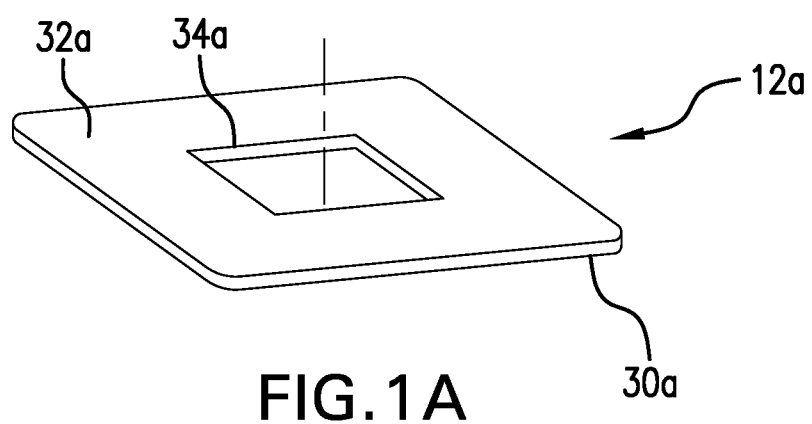
FIG. 1A is a schematic exploded perspective view of a skin contacting element according to an alternate exemplary embodiment.

Alternatively, as shown in FIG. 1A, skin contacting element 12a can be substituted for skin contacting element 12 and can include a single opening 34a extending through the skin contacting element 12a from skin contacting side 30a to interface side 32a. The opening 34a can be arranged for positioning at (e.g., over or around) the tissue site 20. Optionally, the skin contacting element 12a and/or the single opening 34a can be dimensioned to fit around the wound portion 20a of the tissue site 20. In one exemplary application, the skin contacting element 12a can be used and left in place when desirable to change the wicking element 36 (e.g., to a fresh wicking element) and/or to change the reactor 16.

The wound contact element 18, also referred to herein as a wound contact layer, can be perforated or formed as an open mesh that is minimally adherent to breached skin tissue (e.g., the wounded portion 20a at the tissue site 20). In one embodiment, the wound contact element 18 is a loose nylon fabric or an open mesh polyurethane film (e.g., a 1 mm polyurethane film) that is flood coated on an underside 18a thereof with a coating 22 that itself is minimally adherent to breached skin tissue and/or can include an anti-bacterial component (e.g., silver, chlorhexidine gluconate (CHG), etc.). For example, the coating 22 can be or include silicone, nylon, etc.

The wound therapy device 10 can further include a wicking element 36. As will be described in more detail below, the wicking element 36 can absorb exudate from the tissue site 20 when the pressure condition is a negative pressure condition that partially vacuums (e.g., vacuums air or oxygen) from the tissue site 20. The wicking element 36 can have suitable liquid retention properties for absorbing an amount of exudate from the tissue site 20. In one embodiment, the wicking element 36 is formed of a suitable wicking material able to withstand an external pressure of up to about 3 psi (i.e., about 0.2 bar). In the same or another embodiment, the wicking element 36 can maintain its shape under pressure (e.g., at 0.2 bar) or can expand as it absorbs exudate. In all embodiments, the wicking element 36 can be arranged so as to be interposed between the reactor 16 and the tissue site 20 when the wound therapy device 10 is applied to the tissue site 20.

The location of the wicking element 36 relative to the other components of the wound therapy device 10 can vary. For example, the wicking element 36 can be positioned above or below the skin contacting element 12. In the embodiment shown in FIG. 2, the wicking element 36 is positioned above the skin contacting element 12 and below the reactor 14. In this embodiment, the wicking element 36 can be provided together with the reactor element 14 (e.g., positioned between release layer 70 and the reactor 16) or as part of the reactor 14 (e.g., between substrate 80 and lower layer 86), for example. Alternatively, in the embodiment where the wicking element 36 is positioned above the skin contacting element 12, the wicking element can be provided together with the skin contacting element 12 (e.g., between release layer 50 and interface side 32 of the skin contacting element 12, and optionally adhered to the interface side 32) or the wicking element 36 can be provided as a separate element that is assembled onto the skin contacting element (e.g., the wicking element 36 could be individually packaged, removed from its packaging and assembled or stacked onto the interface side 32). In the embodiment shown in FIG. 2A, the wicking element is provided together with the skin contacting element and is interposed between the underside 30 of the skin contacting element 12 and the wound contact element 18.

The wicking element 36 can be sized relative to the one or more openings 34 (or the opening 34a of the skin contacting element 12a). Also, the wicking element 36 can be arranged and sized such that the pressure condition is applied to the tissue site 20, and particularly to the wound portion 20a thereof, through or via the wicking element 36. For example, the wicking element 36 can be larger than the footprint area defined by the one or more openings 34. In the alternative embodiment of FIG. 1A, the openings 34 and the skin contacting element 12a can be similarly shaped to the wicking element 36 and arranged such that the skin contacting element 12a is disposed peripherally about the wicking element 36. For example, the wicking element 36 can be sized to provide an interference fit between the wicking element and the skin contacting element 12a (i.e., the portions of the skin contacting element 12a forming the opening 34a) or can be sized so that there is no gap between an outer periphery of the wicking element 36 and the skin contacting element 12a. Still further, the wicking element 36 could be larger than the opening 34a so as to overlap or underlap the skin contacting element 12a.

Both the skin contacting side 30 and the interface side 32 can be generally flat or planar, though as indicated above the skin contacting element 12 can be flexible and able to conform to the contours at the tissue site 20. In the illustrated embodiment, the interface side 32 is the upper side of the skin contacting element 12 and the skin contacting side 30 is the lower side of the skin contacting element 12 (i.e., lower and thus positioned more closely to the tissue site 20 than the interface side 32). Likewise, the wound contact element 18 can have the underside 18a and an upper side 18b, both of which can be flat or planar, though both can be flexible and able to conform to the contours at the tissue site 20.

Figure 2:
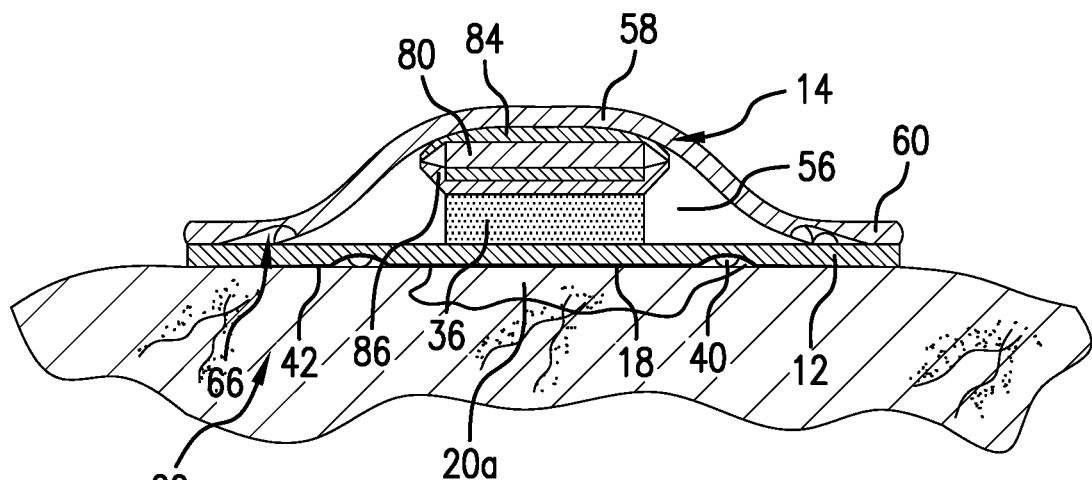
FIG. 2 is a schematic cross-sectional view of the controlled pressure device depicted in FIG. 1.
Figure 2A:
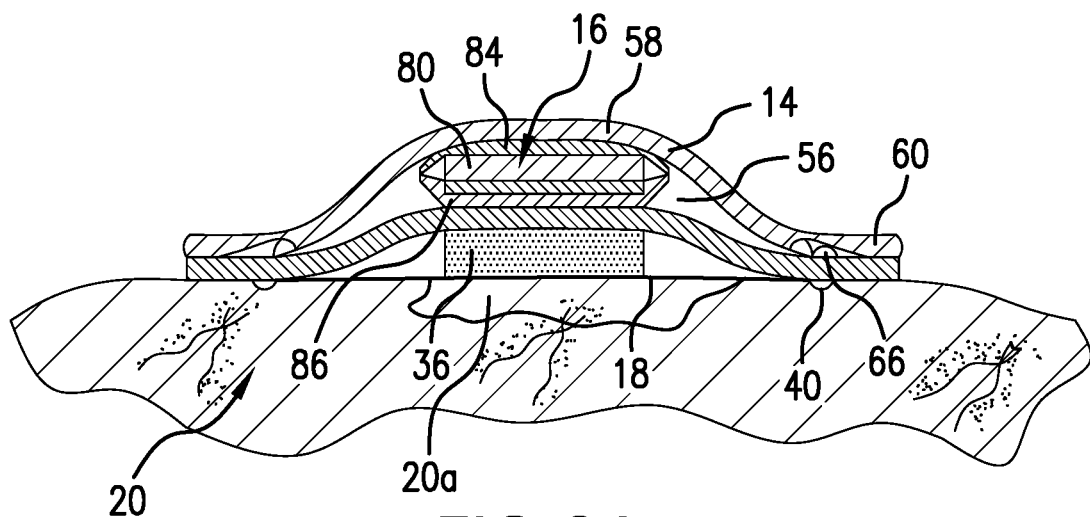
FIG. 2A is a schematic cross-sectional view of a controlled pressure device similar to the one shown in FIG. 2 but according to an alternate exemplary embodiment.

The wound therapy device 10 can further include at least one skin adhering or sealing element (e.g., seal 40 and adhesive 42) disposed on or adjacent the skin contacting side 30 of the skin contacting element 12 for adhering or sealing the skin contacting element 12 to and/or around the tissue site 20. In the illustrated embodiment, the at least one skin adhering or sealing element is or includes perimeter pressure seal 40, also referred to herein as a gasket, that seals the skin contacting element 12 around the tissue site 20 so the pressure condition created by the reactor 16 is applied to the tissue site 20. In particular, as shown in FIG. 2, the perimeter pressure seal 40 can seal the wound contact element 18 and the skin contacting element 12 to the tissue site 20. In addition, or in the alternative, the at least one skin adhering or sealing element is or includes adhesive 42 adhering the skin contacting element 12 to and/or around the tissue site 20. In particular, as shown in FIG. 2, the adhesive 42 is provided peripherally around the perimeter pressure seal to adhere the skin contacting element 12 to the tissue site 20.

The seal or gasket 40 can be made from a hydrogel to further promote sealing around the tissue site 20 and thereby promote the pressure condition (e.g., topical negative pressure) at the tissue site 20. The adhesive 42 can be a biocompatible acrylic adhesive, for example, that is flood coated onto the skin contacting side 30 of the skin contacting element 12. In one embodiment, the adhesive 42 is formed as a layer on the skin contacting side 30 of the skin contacting element 12 (e.g., flood coated thereon), the wound contact element 18 is overlaid onto the skin contact side 30 and the seal 40 is applied as a perimeter bead (e.g., a bead of hydrogel) over the adhesive 42 at the location of a perimeter edge 18c of the wound contact element 18. The size and/or width of the seal 40 can vary. In alternate embodiment, not shown, the seal 40 can be provided as a plurality of seals, such as a plurality of concentric rings for example.

To protect and/or package the skin contacting element 12 and the wound contact element 18 (and optionally the wicking element 36), a first skin contacting element release layer 44, also referred to herein as a tear-off barrier element, can be provided with the wound therapy device 10 to protect the skin contacting side 30 of the skin contacting element 12, the underside 18a of the wound contact element 18 and optionally the wicking element 36 (i.e., when the wicking element 36 is provided together with the skin contacting element 12). In particular, the release layer 44 can be disposed over the skin contacting side 30 of the skin contacting element 12 and over the wound contact element 18. The release layer 44 can be removable to expose the adhesive 42 and/or the perimeter pressure seal 40 provided on the skin contacting side 30 of the skin contacting element 12. The release layer 44 can be similar to known release layers and includes an upper side 46 that is releasable from the skin contacting side 30 of the skin contacting element 12. The release layer 44 can also include a lower side 48 opposite the upper side 46. In one embodiment, the release layer 44 is removably secured to the skin contacting side 30 via a polyurethane film (not shown). Optionally, no seal 40 is provided beneath the release layer 44 but is later applied after the release layer 44 is removed.

Also optionally, a second skin contacting element release layer 50, also referred to herein as an interface side release layer, can be provided with the wound therapy device 10 to protect the interface side 32 of the skin contacting element 12 and the wicking element 36. In particular, the release layer 50 can be disposed over the interface side 32 of the skin contacting element to provide the skin contacting element as a first package component that is separate from the reactor housing element 14 and the reactor 16, which can together be provided as a second package component. For example, the release layer 50 can be provided with the skin contacting element 12 and the wound contact element 18 are separately provided and/or packaged relative the reactor housing element 14 and the reactor 16. The release layer 50 can be like the release layer 44. For example, the release layer 50 can be disposed over the interface side 32 of the skin contacting element. The release layer 50 can be removable to expose the interface side 32. More particularly, the release layer 50 can include an upper side 52 and a lower side 54 opposite the upper side 52 that is releasable from the interface side 32 of the skin contacting element 12. Optionally, when the wicking element 36 is provided and/or packaged together with the skin contacting element 12, the release layer 50 can also protect the wicking element 36.

The reactor housing element 14 cooperates with the skin contacting element 12 to define an enclosed volume 56 around and/or at the tissue site 20 when the skin contacting side 30 of the skin contacting element 12 is in contact with the subject's skin (i.e., adhered around and/or at the tissue site 20, and particularly around and/or at the wound portion 20a). Accordingly, in the illustrated embodiment, the reactor housing element 14 defines the enclosed volume 56 in which the reactor 16 is accommodated. The reactor housing element 14 of the illustrated embodiment includes a hood or hood portion 58 and a lower peripheral section 60. In the illustrated embodiment, the lower peripheral section 60 entirely surrounds the hood 58, which is raised in relation to the lower peripheral section 60 so as to define the enclosed volume 56 around and/or at the tissue site 20 when the skin contacting element 12 is in contact with the subject's skin. The reactor housing element 14 can be made from a material that is air impermeable or partially impermeable so that air is precluded or greatly inhibited from entering into the enclosed volume 56 as the reactor 16 consumes one or more selected gases within the enclosed volume 56 and thereby reducing gas pressure within the enclosed volume 56.

In alternate embodiments, the reactor housing element 14 can be made from materials that are at least partially impervious to particular gasses (e.g., oxygen) and at least partially pervious to other gases (e.g., carbon dioxide, nitrogen, etc.). For example, the reactor housing element 14 can be made from a material that exhausts a higher ratio of certain gases relative to other gases than would occur with direct communication to ambient. Optionally, for example, the reactor housing element 14 can be formed of a material that is at least partially (or is more) gas permeable for selected gasses (e.g., nitrogen or carbon dioxide gas permeable) relative to other gases to exhaust or better exhaust the selected gas from the tissue site 20 to atmosphere.

The reactor housing element 14 can also be formed without the hood 58, i.e., the reactor housing element 14 could at least initially be planar as shown in FIG. 1. Similar to the skin contacting element 12, the reactor housing element 14 can be made from a thin sheet-like membrane, for example using a roll-to-roll process. The reactor housing element 14 can be made from a flexible material that is similar to or the same flexibility as the skin contacting element 12, which allows the wound therapy device 10 to conform to the skin around the tissue site 20. When the reactor housing element 14 is affixed to the skin contacting element 12, the reactor 16 is located between the reactor housing element 14 and the skin contacting element 12. The wicking element 36, which as describe above can be located in one of several different locations in the wound therapy device 10, is interposed between the reactor 16 and the skin contacting element 12. Since the reactor housing element 14 can be made from a flexible material, the section of the reactor housing element 14 that is not in contact with the skin contacting element 12 is raised or offset from the tissue site 20 so as to form the hood 58.

The reactor housing element 14 includes a lower affixing surface or side 62 and an upper side 64, which is opposite the lower affixing side 62. As will be described in further detail below, the reactor housing element 14 can be affixed to the interface side 32 of the skin contacting element 12 providing a substantially air-tight seal between the reactor housing element 14 and the skin contacting element 12. This can preclude air migration between or along an interface between the lower side 62 of the reactor housing element 14 and the interface side 32 of the skin contacting element 12. In one embodiment, the reactor housing element 14 is provided as a separate component relative to the skin contacting element 12. In another embodiment, the reactor housing element 12 is provided already assembled with the skin contacting element 12.

For the interface between the reactor housing element 14 and the skin contacting element 12, the wound therapy device 10 can further include at least one reactor adhering or sealing element (e.g., perimeter pressure seal 66 and/or adhesive 68) interposed between the skin contacting element 12 and the reactor housing element 14 for adhering or sealing the reactor housing element 14 to the skin contacting element 12. In one embodiment, the at least one reactor adhering or sealing element is or includes perimeter pressure seal 66, also referred to herein as a gasket, that seals the reactor housing element 14 to the skin contacting element 12. In the same or an alternate embodiment, the at least one reactor adhering or sealing element includes adhesive 68 adhering the reactor housing element 14 to the skin contacting element 12. The seal 66 can be like the seal 40, including the alternate embodiment(s) described in association with the seal 40. For example, the seal 66 can be made from a hydrogel to further promote sealing between the skin contacting element 12 and the reactor housing element 14 to thereby enhance application of the pressure condition at the tissue site 20 and the adhesive can be formed as layer on the lower affixing side 62 of the lower peripheral section 60 of the reactor housing element 14 with the seal 66 applied as a perimeter bead over the adhesive layer.

When the reactor housing element 14 is separately provided and/or packaged relative to the skin contacting element, the wound therapy device 10 can further include a reactor housing release layer 70 disposed over the lower affixing side 62 of the reactor housing element 14 to protect the lower affixing side 62 and over the reactor 16 to protect the reactor 16 and/or to inhibit actuation of the reactor 16.

The release layer can be the same or similar to the release layers 44, 50. The release layer 70 is removable to expose the reactor 16 accommodated by the reactor housing element 14 to actuate the reactor 16 as will be described in more detail below. The release layer 70 can include an upper side 72 that is releasable from the lower affixing side 62 of the reactor housing element 14 and a lower side 74 opposite the upper side 72.

The reactor 16 can be positioned in the enclosed volume 56 and can be configured to react with at least one selected gas (e.g., nitrogen, oxygen, carbon dioxide, etc.) found in air to consume the at least one selected gas within the enclosed volume 56, which can reduce gas pressure within the enclosed volume 56. The reduction in gas pressure within the enclosed volume 56 can result in a partial vacuum being formed in the enclosed volume 56. As such, the pressure condition created by the reactor 16 upon actuation thereof can be a topical negative pressure applied to the tissue site 20, and particularly to the wound portion 20a thereof (e.g., bar negative pressure after an initial actuation startup period). In one embodiment, the topical negative pressure is a partial oxygen vacuum that absorbs oxygen from the tissue site 20. Optionally, the pressure condition created by the reactor 16 is a negative pressure condition that removes or vacuums oxygen from the tissue site 20 (and particularly the wound portion 20a), and removes at least one other gas (e.g., nitrogen or carbon dioxide) in addition to the oxygen from the tissue site 20. This can have the advantage of more efficiently drawing exudate from the tissue site 20. Also, the negative pressure condition created by the reactor 16 can result in the reactor 16 and thereby the entire wound therapy device 10 being urged toward the tissue site 20. Also advantageous, the limited heat from the reactor can be used to assist in healing at the tissue site (e.g., preventing infection).

More particularly, the reactor 16 can be positioned in the enclosed volume 56 and can be configured to react with a selected gas found in air. In one embodiment, as the reactor 16 consumes the selected gas within the enclosed volume 56, the gas pressure within the enclosed volume 56 is reduced. For example, where the reactor 16 consumes oxygen, there can be an approximate 20% reduction from atmospheric pressure in the enclosed volume 56. An example of a reactor 16 that can be used in the wound therapy device 10 is described in US 2014/0109890 A1, which is incorporated by reference herein. US 2014/0109890 A1 describes an oxygen based heater; however, the oxygen based heater described in US 2014/0109890 A1 can be used as the reactor 16 to consume oxygen within the enclosed volume 56 thus producing a partial vacuum within the enclosed volume 56. In this example, the reactor 16 includes a reducing agent, a catalytic agent for reduction of oxygen such as carbon, a binding agent and a ion conducting solution or an electrolyte solution, which can be applied onto a reactor substrate 80. The reducing agent on the reactor substrate 80 can be zinc, aluminum, or iron, for example. This can be considered a chemical pump and/or a non-electrochemical cell reactor in that no current is flowing therein.

Advantageously, the reactor 16 can be biocompatible. For example, the reactor 16 can be such that it is suitable for using in close proximity and/or contact with a subject's skin. Also for example, the reactor 16 can be pH neutral. For example, the reactor 16 can have a pH that is between about 6 and about 8. Optionally, the reactor 16 (e.g., the reactor substrate 80) can be provided as a flexible reactor. For example, the substrate 80 can include the agents arranged or provided to increase flexibility of the substrate (e.g., the agents could be arranged in rows). As mentioned hereinabove, the reactor 16 can include an electrolyte solution, which can be an aqueous electrolyte solution. This can advantageously facilitate maintenance of a humid environment at the tissue site 20, and particularly at the wound portion 20a thereof. In addition or in the alternative, an aqueous electrolyte solution can be provided within the reactor housing element 14 (e.g., as a gel or absorbed into a separate sponge, not shown).

The release layer 70 on the lower side 62 of the reactor housing element 14 can operate as an air-type barrier such that the selected gas (e.g., nitrogen, oxygen, carbon dioxide, etc.) is precluded from access to the reactor 16 until after an air-tight barrier, which in the illustrated embodiment is the release layer 70, is removed from the reactor housing element 14. Alternatively, the reactor 16 can be provided as a package, which is shown in FIG. 1 as including an upper layer 84 and a lower layer 86. The upper layer 84 affixes to the lower layer 86 to enclose the reactor substrate 80 therebetween so as to provide an air-type seal so that the selected gas is precluded from access to the reactor 16. In this example including the package, the upper layer 84 and/or the lower layer 86 can operate as an air tight barrier and that removal of the upper layer 84 from the lower layer 86, or vice versa, in whole or in part, allows the selected gas (e.g., oxygen) access to the reactor 16 so that the selected gas can be consumed by the reactor 16.

Alternatively, at least one of the layers (the lower layer 86 in the illustrated embodiment) can include openings 88 and a seal layer 90 can be affixed in an air-tight manner to the lower layer 86 covering the openings 88. Removal of the seal layer 90 from the lower layer 86 exposes the reactor 16 to the selected gas via the openings 88, which allows the reactor 16 to consume the selected gas within the enclosed volume 56. The surface area of the openings 88 can be appropriately sized to control the flow of the selected gas through the openings 88. This can sustain the chemical reaction of the reactor 16 to the desirable time limit for maintaining the desired pressure condition on the tissue site 20 for a desired duration (e.g., 12 hours, 24 hours, etc.). In addition or in the alternative, the number and/or size of the openings 88 can be selected to control or limit the rate of consumption of the reactor thereby controlling the pressure condition created by the reactor and/or controlling the amount of heat created by the reactor. In addition or in the alternative, multiple seal layers 90 can be provided so that removal of one or a selected few of the seal layers (while other seal layers are still affixed to the lower layer 86) can also be provided to limit the flow of the selected gas toward the reactor 16.

Additionally, to further control the pressure within the enclosed volume 56, the wound therapy device 10 can include a pressure release valve 92 on the reactor housing element 14, and particularly on the hood 58 of the reactor housing element 14. The pressure release valve 92 can allow for selected communication between the enclosed volume 56 and ambient. The pressure release valve 92 can be operated when a predetermined pressure differential exists between the enclosed volume 56 and ambient.

In one embodiment, the wound therapy device 10 can be packaged such that the reactor housing element 14 and the reactor 16 are packaged separately from the skin contacting element 12, though this is not required. In such an embodiment, the release layers 50 and 70 are removed, respectively, from the skin contacting element 12 and the reactor housing element 14. Removal of the release layer 70, as indicated above, can expose the reactor 16 and thereby actuate the reactor 16. Optionally, the release layer 70 can be affixed to the lower layer 86 such that removal of the release layer 70 from the reactor housing element 14 results in removal of the lower layer 86 from the upper layer 84 thereby exposing the reactor 16 to actuate the reactor 16. Alternatively, the release layer 70 can be affixed to the seal layer 90 such that removal of the release layer 70 from the reactor housing element 14 results in removal of the seal layer or layers 90 from the lower layer 86, thus exposing the reactor 16 to air via the openings 88 provided in the lower layer 86. After removal of the release layer 70 from the reactor housing element 14, the lower side 62 of the reactor housing element 14 can be brought into contact with the interface side 32 of the skin contacting element 12 providing a substantially air-tight seal between the reactor housing element 14 and the skin contacting element 12, such as via the seal 66 and the adhesive 68.

Additionally, the reactor housing element 14 can include a liquid impermeable-air permeable membrane 100, also referred to herein as an air permeable liquid impervious membrane, arranged on an exposure side of the reactor 16 (i.e., the side facing the tissue site 20) so as to be interposed between the reactor 16 and the skin contacting element 12 (e.g., when the reactor housing element 14 is affixed to the skin contacting element 12). The membrane 100 can function to inhibit or limit exudate suctioned from the tissue site 20 from reaching the reactor 16, particularly the reactor substrate 80, thereby hindering the effectiveness or operational capabilities of the reactor 16. The size (i.e., surface area) of the liquid impermeable-air permeable membrane 100 can depend on the location of the liquid impermeable-air permeable membrane 100 within the wound therapy device 10. If exudate from the tissue site 20 were to come in contact with the reactor substrate 80, the chemical reaction of the reactor 16 when coming in contact with the selected gas may be impaired. As such, the membrane 100 allows airflow between the tissue site 20 and the reactor 16 while precluding or at least inhibiting exudate from coming in contact with the reactor 16. By way of example, the membrane 100 can be a polytetrafluoroethylene film, such as Gore-Tex® or a similar material.

The liquid impermeable-air permeable membrane 100 can be located in different locations in the wound therapy device 10. In one example, the liquid impermeable-air permeable membrane 100 can be located between the reactor substrate 80 and the lower layer 86 making up the air-tight package for the reactor 16. So, once the lower layer 86 (or the seal layer 90) is removed, air can gain access to the reactor 16, but exudate from the tissue site 20 would be precluded or at least inhibited from traveling through the liquid impermeable-air permeable membrane 100. In another example, liquid impermeable-air permeable membrane 100 can be located between the lower layer 86 (or the seal layer 90) making up the air-tight package for the reactor 16 and wicking element 36.

In an embodiment where the reactor housing element 14 and the reactor 16 are packaged separately from the skin contacting element 12, the release layer can be removed from the reactor housing element 14. Removal of the release layer 70 from the reactor housing element 14 can expose the reactor 16 to air by removal of the lower layer 86, the seal layer 90, or the release layer 70 may be affixed in an air-tight manner to the reactor housing element 14 so that air is precluded from access to the reactor 16 until after the release layer 70 is removed from the reactor housing element 14. After removal of the release layer 70 from the reactor housing element 14, the lower side 62 of the reactor housing element 14 can be affixed to the skin contacting element 12 (e.g., after release layer 50 is removed from the skin contacting element 12).

In an alternate embodiment, the wound therapy device 10 can come pre-assembled with the reactor housing element 14 already affixed to the skin contacting element 12. In this embodiment, the release 70 can be excluded and the lower layer 86, when included, can be provided to allow communication therethrough to the reactor 16 (e.g., the seal layer 90 can be excluded). Removal of the release layer 44 can function to actuate the reactor 16.

In a further embodiment, the reactor housing element 14 and the reactor 16 can be removably affixed to the skin contacting element 12 to enable replacement of the reactor housing element 14 and the reactor 16 without removing the skin contacting element 12 from the tissue site. In addition, the wicking element 36 can be removable from the skin contacting element 12 after the skin contacting element 12 is adhered to the tissue site for replacement of the wicking element 36 (e.g., when the wicking element is saturated beyond a predetermined amount with exudate). In one example, the reactor housing element 14, the reactor 16 and the wicking element 36 can be simultaneously replaced without replacement of the skin contacting element 12. In another embodiment, only one or other of the reactor housing element 14 (and reactor 16) or the wicking element 36 can be removed and replaced.

In any embodiment, the wound therapy device 10 can be designed to account for certain operating and/or design parameters. Such parameters can include, for example, the maximum exudate volume to be contained by the wound therapy device 10 (e.g., by the wicking element 36), the rate of exudate removed from the tissue site, the amount of time to reach a preferred negative pressure (e.g., 0.2 bar negative pressure), the service time for the wound therapy device 10 (i.e., amount of time between bandage changes), the expected efficiency/utilization of the reducing agent of the reactor substrate 80 (e.g., zinc), the amount of the reducing agent (and thus the gas scavenging capacity of the device 10), etc. As an example, assuming the tissue site 20 of about 10 cm×20 cm and an offset of the hood 58 (or the top of the reactor housing element 14) of about 2.5 cm from the tissue site 20 results in the enclosed volume 56 of approximately 500 mL. Assuming that the wicking element 36 and any other solid components (e.g., the liquid impermeable-air permeable membrane 100) within the enclosed volume 56 account for 100 mL within the enclosed volume 56 (and prior to any exudate being drawn into the enclosed volume 56) there could be 400 mL air in the enclosed volume 56. The 400 mL of air comprises about 320 mL of nitrogen and about 80 mL of oxygen at standard temperature and pressure (STP) within the enclosed volume 56 prior to the application of a partial vacuum from the reactor 16 consuming a selected gas in the air within the enclosed volume 56 and prior to any exudate being sucked into the device 10. In actual application, the size of the tissue site 20, the offset and the enclosed volume can vary and may be much smaller than the example above.

One gram (1 g) of zinc (Zn) has the capacity to consume about 170 mL at STP of oxygen ($O_2$), which is the amount of oxygen in about 850 mL (STP) of normal dry air. Although the seals 40, 66 can be provided, there can be leakage of ambient air into the enclosed volume 56 past the seals 40, 66 and can be diffusion through the reactor housing element 14 and the skin contacting element 12. For the purposes of this disclosure, both leakage past interfaces (e.g., leakage around the seal 40) and diffusion (e.g., diffusion through the reactor housing element 14) will be referred to as leakage. The seals 40, 66, the skin contacting element 12 and reactor housing element 14 can be configured to have a maximum leakage rate of air into the enclosed volume 56 from ambient. For example, a maximum leakage rate of 1 mL (STP)/hour of air into the enclosed volume from ambient results in of oxygen/hour. Since 1 g of zinc consumes 170 mL of oxygen (STP), 1 g of zinc provides an adequate amount of a reducing agent to result in a 20% reduction from normal atmospheric pressure within the enclosed volume 56 for an extended period of time, e.g., well over 72 hours. This accounts for exudate being sucked into the device 10 from the tissue site at a rate of about 0.5 mL to 1 mL per hour. As will be understood by those with ordinary skill in the art, the reactor 16 may not operate to give full utilization of a given amount of the reducing agent and so an efficiency factor may need to be accounted for.

In view of the foregoing, and only by way of illustrative example, the wound therapy device 10 can be configured as follows. The reactor 16 can be configured to have a predetermined scavenging capacity ("SC"), which relates to the volume of the selected gas that the reactor 16 is configured to consume. For example, as mentioned above, 1 g of zinc will consume about 170 mL of oxygen (STP), so the scavenging capacity would be 170 mL. The enclosed volume 56 can have a determined volume ("DV") based on the area of the tissue site 20, the size of the reactor housing element 14, the offset of the hood 58 (or the top of the reactor housing element 14) from the tissue site 20, taking into account the wicking element 36 in addition to the reactor 16 and any other solid components within the enclosed volume 56. For example, the determined volume of 400 mL was discussed above. Also, the wound therapy device 10 can be configured to have a maximum leakage rate (LR) for air entering the enclosed volume 56. In addition, the wound therapy device 10 can be configured to have a minimum wear time ("MWT"), which relates to the minimum amount of time that the wound therapy device 10 is configured to be worn. Assuming that it is desirable to have the reactor 16 consume, or scavenge, the selected gas for the entire minimum wear time, the wound therapy device can be configured in view of the following relationship:

$$SC > DV * (\% \text{ of selected gas in air}) + LR * (\% \text{ of selected gas in air}) * MWT.$$

The scavenging capacity can be determined to provide a relatively small reactor 16 in relation to the reactor housing element 14 and the tissue site 20 to be treated. The determined volume can be determined to provide a relatively small reactor 16 and reactor housing element 14 in view the tissue site 20 to be treated. The maximum leakage rate for air entering the enclosed volume 56 can be reduced as much as is practical; however, there may be some circumstances in which a predetermined amount of leakage is desirable, for example where cycling of pressure within the enclosed volume 56 is desired. For example, the maximum leakage rate for air entering the enclosed volume 56 can be less than 10 mL/hour, and preferably less than 1 or 2 mL/hr. The minimum wear time can be determined based on the desired amount of time the topical negative pressure is to be applied to the tissue site 20. For example, the minimum wear time can be equal to or greater than 72 hours, equal to or greater than 48 hours, equal to or greater than 24 hours, equal to or greater than 12 hours, equal to or greater than 8 hours, or equal to or greater than 4 hours. It may be desirable to include a safety factor (e.g., a multiplier on the right side of the relationship above) to accommodate for manufacturing tolerances, differences among tissues sites and persons placing the wound therapy device 10 on the tissue site 20.

As the reactor 16 consumes the selected gas found in air within the enclosed volume 56, an exothermic reaction occurs such that the reactor 16 consumes the selected gas within the enclosed volume 56. The gas pressure within the enclosed volume 56 is reduced, for example, where the reactor 16 consumes oxygen, there can be an approximate 20% reduction from atmospheric pressure in the enclosed volume 56. The electrolyte chosen for the reactor 16 can be one that is able to sustain a 0.8 bar pressure (i.e., 0.2 bar negative pressure or about 150 mmHg) within the enclosed volume for up to 8 hours, preferably for up to 12 hours, and in more preferably up to 24-72 hours.

Optionally, the reactor housing element 14 could also be provided with a removable section 160 that when removed could provide access to the reactor 16. This could enable replacement of the reactor 16 independent of the reactor housing element 14. Alternatively, the removable section could enable additional ambient air access to the reactor 16 or an additional reactor located beneath the reactor housing element 14. For example, the removable section 160 can be affixed to the upper layer 84 of the package in which the reactor substrate 80 is located. Removal of the removable section 160 can result in removal of at least a portion of the upper layer 84 thus exposing the reactor substrate 80 to ambient air, which would result in an exothermic reaction. Alternatively, an additional reactor (not shown) could be located beneath the reactor housing element 14 and removal of the removable section 160 can result in removal of at least a portion of the package (similar to the package made up of the upper layer 84 and the lower layer 86) thus exposing the additional reactor to ambient air.

Figure 3:
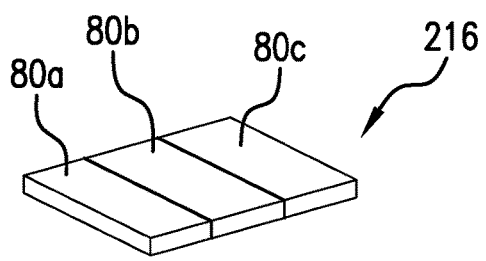
FIGS. 3 and 4 schematically depict reactors according to an alternate exemplary embodiments.

Different types of reactors could be used to provide topical negative pressure inside the enclosed volume 56 of the wound therapy device 10. FIG. 3 depicts a reactor 216 that can be used in place of the reactor 16 shown in FIG. 1. The reactor 216 can include multiple reactor substrates or multiple regions on the same reactor substrate, which are depicted as reactor elements 80a, 80b and 80c each having different chemical properties and/or characteristics. For example, the first reactor element 80a can be configured to begin consuming oxygen after being exposed to oxygen for a very short (first) period of time t1, e.g., nearly instantaneously. The second reactor element 80b can be configured to begin consuming oxygen after being exposed to oxygen for a longer (second) period of time t2, and the third reactor element 80c can be configured to begin consuming oxygen after being exposed to oxygen for an even longer (third) period of time. Such a configuration can allow for a cycling of pressure in the enclosed volume 56.

In lieu of the reactor 16 made up of the reactor substrate 80, the reactor 16 may be one or any combination of electro-chemical pumps, vacuum-on-demand devices (referred to herein as VOD), electrolyzers, pressure-reducing solid state devices, oxygen absorbing iron packets, or getters of zirconium titanium, vanadium iron, lithium, lithium metal, magnesium, calcium, lithium barium combinations, zinc-air battery, zinc-air battery components or other materials highly reactive with the selected gases, for example, nitrogen, carbon dioxide and oxygen gases found in wound bed environments.

Figure 4:
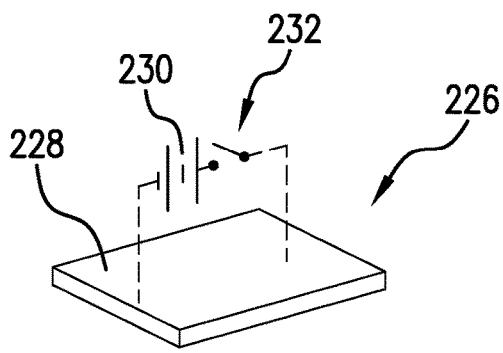

FIG. 4 depicts another reactor 226 that can be used in place of the reactor 16 shown in FIG. 1. WO 2015/054040 A1, which is incorporated by reference, describes an electrochemical cell that is adapted to consume gases, i.e., air or its gaseous non-noble constituents, within an enclosure via an electrochemical reaction. This consumption of gas within a sealed enclosure forms a partial vacuum. The wound therapy device 10 can include such a reactor 226 having an electrochemical cell 228 that lowers the pressure within the enclosed volume 56 through an electrochemical reaction that takes place when a voltage is applied to the electrochemical cell 228 by a power source 230 (depicted schematically in FIG. 4). Operation of electrochemical cell 228 in this example can also be achieved by controlling the current supplied to the electrochemical cell 228 by the power source 230, for example by providing a switch 232 that can be operated by the user. The power source 230 can be located in the enclosed volume 56 or be provided outside the wound therapy device 10 (e.g. on the reactor housing element 14). The switch 232 can be provided outside the wound therapy device 10 (e.g. on the reactor housing element 14).

In an example where the reactor is a VOD device, a VOD is a solid state electrochemical cell, which when charged with a low current, produces a highly reactive material that captures gases present in the atmosphere and when sealed in an air tight system can form a partial vacuum. In a VOD device, metal is deposited to grow dendrites as a voltage is applied across electrodes of the VOD device and lithium salt electrolyte, charging the VOD device. Similar to charging a battery, electrons are moved from layer to layer to form metallic lithium.

In an example where the reactor is a getter, a getter, as known in the art, is a deposit of reactor material that is used for initiating and maintaining a partial vacuum. When gas molecules strike the getter material, particular gas molecules (i.e., those of the selected gas) combine with the getter chemically or by adsorption. Thus the getter removes the selected gas from the evacuated space until the active material is exhausted.

A reactor having a self-regulating oxygen getter powered by zinc-air battery technology may be used in lieu of the above-described reactor 16 made up of the reactor substrate 80. Zinc-air batteries can react to control or reduce the oxygen levels in sealed site and thus self-regulate a partial vacuum pressure of approximately 0.8 bars. If the zinc-air battery components are configured as a working zinc-air battery, the battery voltage will drop when the oxygen has been depleted and the desired vacuum pressure will have been achieved. This drop in voltage may be used to indicate that the desired partial vacuum has been achieved. For example, a 675 size hearing aid zinc-air battery is rated at 620 mAh, occupies mL volume, and weighs 1.9 g. A 675 zinc-air battery can remove more than 150 times its volume of oxygen.

The wound therapy device 10 can also include additional powered components, which is shown as a powered component 240 that is schematically depicted in FIG. 1. Each powered component 240, which are described later with reference to FIGS. 5-7, can be electrically connected with a power source 242 (depicted schematically in FIG. 1) which, for example, can be a zinc-air battery exposed to ambient and electrically connected with the powered component 240. When using a zinc-air battery as the power source 242, the power source 242 would be located outside of the enclosed volume 56 or a section of the reactor housing element 14 or the skin contacting element 12 could be removable to allow ambient air to contact the zinc-air battery.

Figure 5:
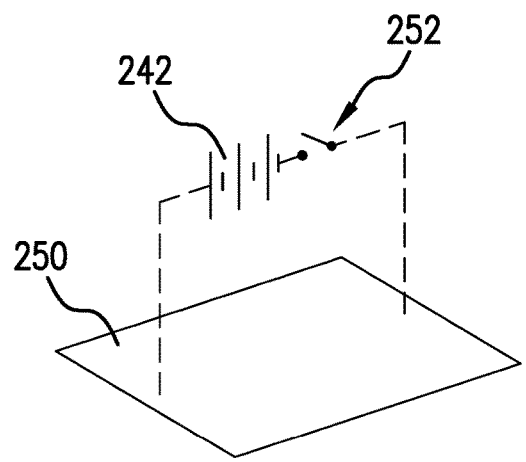
FIGS. 5-7 schematically depict powered components according to alternate exemplary embodiments for use with the controlled pressure device of FIG. 1.

FIG. 5 depicts a heater 250, which is one example of a powered component 240 that can be used in the wound therapy device 10, electrically connected with the power source 242. The heater 250 can be a thin film heater. The heater 250 can provide heat for purposes of reducing the likelihood of infection at the tissue site 20. A switch 252 can be provided to control power to the heater 250.

Figure 6:
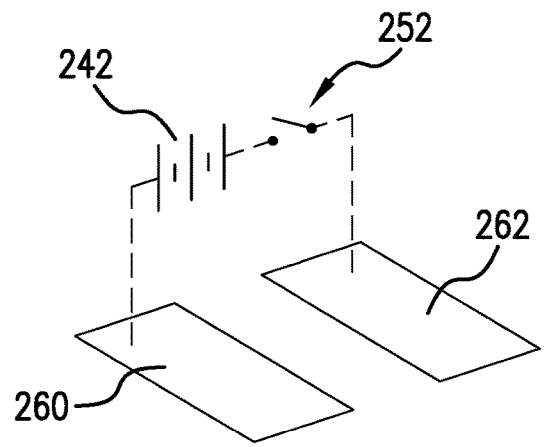

FIG. 6 depicts a first electrode 260 and a second electrode 262 electrically connected with the power source 242. The electrodes are another example of a powered component 240 that can be used in the wound therapy device 10. The switch 252 can be provided to control power to the electrodes 260, 262. The first electrode 260 can be positioned on a first side of the tissue site 20 and in contact with the skin, and the second electrode 262 can be positioned on a second, opposite, side of the tissue site 20 and in contact with the skin. The electrodes 260, 262 can be used to provide electrical stimulation to the tissue site 20.

Figure 7:
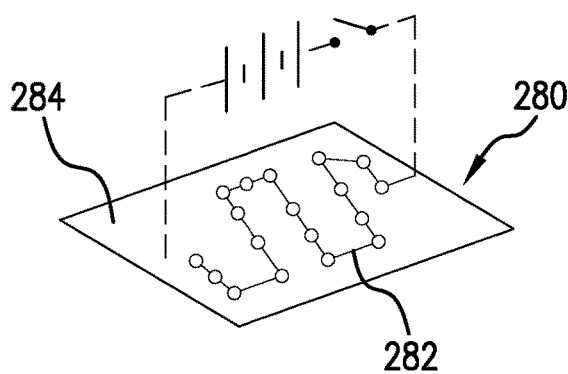

FIG. 7 depicts a light source 280, which is another example of a powered component 240 that can be used in the wound therapy device 10. The light source 280 can include a plurality of LEDs 282 mounted on a flexible substrate 284. The LEDs 282 are electrically connected with the power source 242. The flexible substrate 284 can be placed adjacent to the skin contacting element 12, which can include larger openings 34, which can allow light to pass for phototherapy. Alternatively, the light source could be used to indicate that a partial vacuum condition exists within the enclosed volume 56.

Optionally, the electrically powered device 240 could be a transceiver, receiver or transmitter to enable wireless communication from the wound therapy device. Also, instead of a the powered device 240, an RFID or non-powered indicator (both not shown) could be embedded with the reactor 14 in the reactor housing element 14.

Optionally, though not shown, the wound therapy device 10 can include an indicator that shows a state of the pressure condition created by the reactor 16. For example, one or more of the wicking element 36, the reactor 14 or the skin contacting element 12 can include a rigid portion that protrudes or causes a raised indicator portion to be shown through the reactor housing element 14. When the reactor 14 creates a negative pressure condition for example, the rigid portion will protrude or show through the reactor housing element 14 to indicate that a partial vacuum condition exists inside the enclosed volume 56. In one embodiment, the rigid portion can be one or more beads disposed in the wicking element 36 (and the wicking element 36 protrudes peripherally about the reactor 140 or disposed above the reactor 16.

Figure 8:
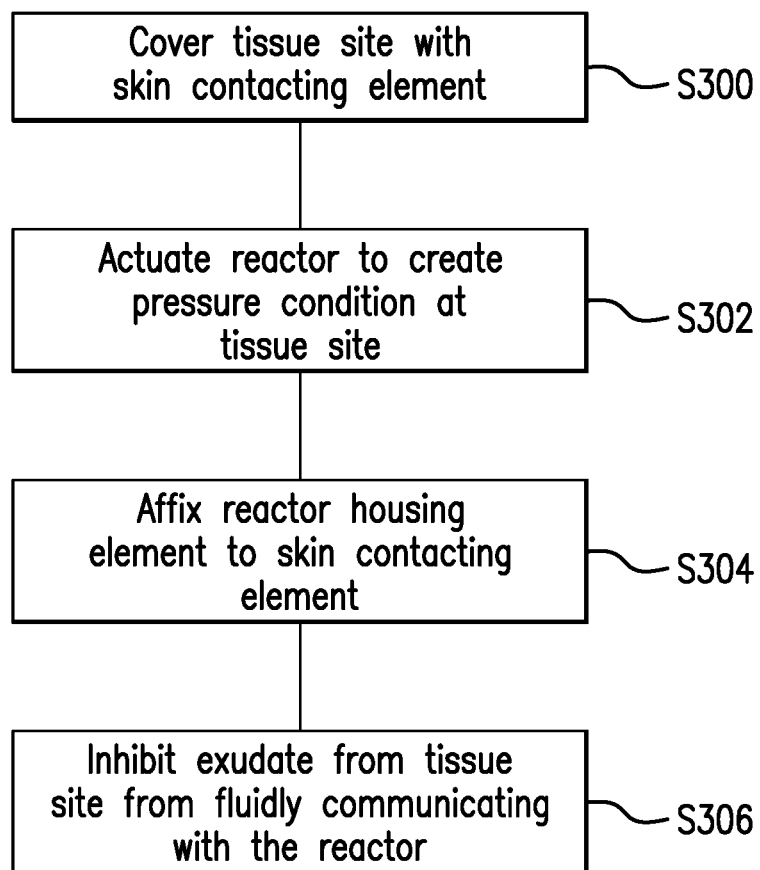
FIG. 8 is a block diagram of a method for applying controlled pressure to a tissue site according to an exemplary embodiment.

A method for applying wound therapy to a tissue site will now be described. In particular, the method will be described in association with the wound therapy device 10 described hereinabove, though it is to be appreciated that other wound therapy devices could be used. In the method, with reference to FIG. 8, the tissue site 20 is covered with the skin contacting element 12 at S300. As already described above, the skin contacting element 12 has a skin contacting side 30 and an interface side 32, which is opposite the skin contacting side 30. This covering of the tissue site 20 with the skin contacting element 12 further includes the skin contacting side 30 being arranged to face the tissue site 20.

At S302, the reactor 16 is actuated to create the pressure condition at the tissue site 20. As already described herein, actuating of the reactor 16 can include creating a negative pressure condition at the tissue site 20. This can provide a suction or partial vacuum force at the tissue site 20 wherein exudate is vacuumed or sucked away from the tissue site 20 into the wound therapy device 10. As mentioned above, the skin contacting element 12 can include the wicking element 36 that absorbs the exudate from the tissue site 20 when the exudate is sucked or vacuumed away from the tissue site 20.

In particular, the pressure condition can be a negative pressure condition wherein oxygen is vacuumed from the tissue site 20. Optionally, the negative pressure condition can also vacuum at least one other gas (e.g., nitrogen, carbon dioxide, etc., or any combination thereof) from the tissue site 20 other than oxygen.

If not already assembled, next at S304, the reactor housing element 14 having the reactor 16 accommodated therein, is affixed to the skin contacting element 12. As already described herein, the reactor housing element 14 has the lower affixing side 62 and the upper side 64, which is opposite the lower affixing side 62. In one embodiment, the affixing of the reactor housing element 14 to the skin contacting element 12 occurs after the actuating of the reactor 16.

As discussed hereinabove, the wound therapy device 10 can include the membrane 100. When so included, the method can further include inhibiting exudate from the tissue site 20 from fluidly communicating with the reactor 16 as indicated at S306. In particular, the membrane 100 inhibits, reduces the likelihood and/or prevents exudate from the tissue site 20 from being vacuumed through (e.g., through the wicking element 36) and into contact with the reactor substrate 80 and the reactor pad 82.

Optionally, the method could include removal and replacement of the reactor housing element 14 and the reactor 16 together. In addition or in the alternative, the method could also include removal and replacement of the wicking element 36. This could occur together with the reactor housing element 14 and the reactor 16 or by itself. For example, the reactor housing element 14 and the reactor 16 could be temporarily unfixed from the skin contacting element 12, the wicking element 36 replaced and then the reactor housing element 14 and the reactor 16 re-affixed to the skin contacting element 12. In these examples, the skin contacting element 12 can remain adhered to the tissue site 20 and avoid undesirable disruptions at the tissue site 20. Also, as described hereinabove, the reactor 16 alone or together with the wicking element 36 could be replaced and the reactor housing element 14 re-affixed to the skin contacting element 12.

In a particular embodiment, use of the wound therapy device 10 can occur as follows. The release layer 44 can be removed from the skin contacting element 12 to expose the adhesive 42 and optionally the perimeter pressure seal 40. Alternatively, after removal of the release layer 44, the perimeter pressure seal 40 can be added to the skin contacting side 30 of the skin contacting element 12. Covering the tissue site with the skin contacting element in S300 can further include adhering and/or sealing the skin contacting element 12 to and/or around the tissue site 20. In particular, such adhering and/or sealing can include both sealing and adhering via the perimeter pressure seal 40 and the adhesive 42.

With the skin contacting element 12 adhered to the tissue site 20 (or around the tissue site 20), the release layer 50 can be removed from the interface side 32 of the skin contacting element 12 and the release layer 70 can be removed from the lower side 62 of the reactor housing element 14. Removal of the release layer 70 can also include, as already described herein, actuation of the reactor 16 accommodated by the reactor housing element 14. Removal of the release layer 70 from the reactor housing element 14 can also function to expose the adhesive 68 provided on the lower side 62 of the reactor housing element 14 and optionally the perimeter pressure seal 66. Alternatively, the perimeter pressure seal 66 can be applied or provided onto the lower side 62 of the reactor housing element 14 after the release layer 70 is removed. Affixing the reactor housing element 14 to the skin contacting element 12 in S304 can further include adhering and/or sealing the reactor housing element 14 to the skin contacting element 12. Specifically, such adhering and/or sealing of the reactor housing element 14 to the skin contacting element 12 can include both sealing and adhering via the perimeter pressure seal 66 and the adhesive 68.

Optionally, the method can further include the exhausting of a gas (e.g., nitrogen, carbon dioxide, etc., or any combination thereof) from the reactor housing element 14 to atmosphere via the reactor housing element 14 being at least partially gas permeable for a particular gas (e.g., at least partially carbon dioxide or nitrogen-gas permeable).

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A wound therapy device, comprising:
   a reactor housing element including a lower side and a first adhesive on the lower side;
   a reactor, which is an oxygen scavenger, for creating a negative pressure condition at an associated tissue site upon actuation thereof disposed beneath the reactor housing element;
   a reactor housing release layer disposed over the first adhesive on the lower side of the reactor housing element, wherein the reactor is positioned between the reactor housing element and the reactor housing release layer, wherein the reactor housing release layer is removable from the lower side of the reactor housing element;
   a skin contacting element configured for covering the associated tissue site, the skin contacting element having a skin contacting side, an interface side, which is opposite the skin contacting side, and at least one opening, wherein the lower side of the reactor housing element is configured to be adhered to the interface side of the skin contacting element after the reactor housing release layer is removed from the lower side of the reactor housing element;
   a seal interposed between the reactor housing element and the skin contacting element when the reactor housing element is adhered to the skin contacting element, the seal providing a substantially air-tight seal between the reactor housing element and the skin contacting element; and
   a wicking element disposed under the skin contacting element.

2. The wound therapy device of claim 1, wherein the reactor housing element is a thin sheet-like membrane.

3. The wound therapy device of claim 1, wherein the skin contacting element is a thin sheet-like membrane.

4. The wound therapy device of claim 1, further including:
   a second adhesive and a gasket disposed on the skin contacting side of the skin contacting element wherein the second adhesive is provided peripherally around to the outside of the gasket.

5. The wound therapy device of claim 1, further including:
   a package including at least one air-tight barrier selectively removable from the package, wherein the reactor is positioned within the package and air is precluded from access to the reactor until after the at least one air-tight barrier is removed from the package.

6. The wound therapy device of claim 1, wherein the reactor housing release layer is removable to expose the reactor to actuate the reactor by exposing the reactor to ambient.

7. The wound therapy device of claim 1, further comprising a wound contact layer, wherein the wicking element is disposed between the skin contacting side of the skin contacting element and a wound contact element.

8. The wound therapy device of claim 7, wherein the wound contact element is minimally adherent to breached skin tissue and/or includes an anti-bacterial component.

9. The wound therapy device of claim 1, further including:
a skin contacting element release layer disposed over the skin contacting side of the skin contacting element, the skin contacting element release layer removable to expose a second adhesive provided on the skin contacting side of the skin contacting element.

10. The wound therapy device of claim 1, wherein the reactor is configured having a predetermined scavenging capacity (SC) for a selected gas, wherein an enclosed volume defined by the reactor housing element in which the reactor is accommodated has a determined volume (DV), the wound therapy device is configured to have a maximum leakage rate (LR) for air entering the enclosed volume, and the wound therapy device is configured to a minimum wear time (MWT) wherein:

$$SC > DV*(\% \text{ of selected gas in air}) + LR*(\% \text{ of selected gas in air})*MWT.$$

11. The wound therapy device of claim 1 wherein the reactor housing element is removably affixed to the skin contacting element to enable removal of the reactor housing element and replacement of one or both of the reactor and the reactor housing element.

12. The wound therapy device of claim 1, further including a pressure release valve disposed on the reactor housing element.

13. A method for applying controlled pressure to a tissue site, comprising:
covering the tissue site with a skin contacting element, the skin contacting element having a skin contacting side, an interface side, which is opposite the skin contacting side, and an opening, the covering of the tissue site with the skin contacting element includes the skin contacting side being arranged to face the tissue site;
removing a reactor housing release layer from a lower side of a reactor housing element;
actuating a reactor, which is an oxygen scavenger, by exposing the oxygen scavenger to air; and
affixing the reactor housing element to the skin contacting element with the reactor disposed between the reactor housing element and the skin contacting element.

14. The method of claim 13, wherein affixing of the reactor housing element to the skin contacting element occurs after actuating of the reactor.

15. The method of claim 13, wherein covering the tissue site with the skin contacting element further includes adhering and sealing the skin contacting element around the tissue site.

16. The method of claim 13, wherein affixing the reactor housing element to the skin contacting element further includes adhering and sealing the reactor housing element to the skin contacting element.

* * * * *